US010300245B2

(12) United States Patent
Finkelstein et al.

(10) Patent No.: US 10,300,245 B2
(45) Date of Patent: May 28, 2019

(54) THERAPEUTIC AGENT APPLICATORS AND METHODS OF USING THE SAME

(75) Inventors: Steven E. Finkelstein, Scottsdale, AZ (US); Matthew C. Biagioli, Tampa, FL (US); Mayer N. Fishman, Tampa, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 0 days.

(21) Appl. No.: 14/128,169

(22) PCT Filed: Jun. 21, 2012

(86) PCT No.: PCT/US2012/043467
§ 371 (c)(1),
(2), (4) Date: Dec. 20, 2013

(87) PCT Pub. No.: WO2012/177827
PCT Pub. Date: Dec. 27, 2012

(65) Prior Publication Data
US 2014/0179979 A1    Jun. 26, 2014

Related U.S. Application Data

(60) Provisional application No. 61/499,510, filed on Jun. 21, 2011.

(51) Int. Cl.
*A61N 5/10*     (2006.01)
*A61M 25/10*    (2013.01)
*A61M 25/00*    (2006.01)

(52) U.S. Cl.
CPC ........ *A61M 25/0043* (2013.01); *A61M 25/10* (2013.01); *A61N 5/1007* (2013.01); *A61M 25/007* (2013.01); *A61N 2005/1008* (2013.01)

(58) Field of Classification Search
CPC ...... A61N 5/10; A61N 5/1001; A61N 5/1002; A61N 5/1007; A61N 5/1014–5/1017; A61N 5/1027; A61N 5/1028; A61M 25/007; A61M 25/0071; A61M 2025/0004; A61M 25/008
See application file for complete search history.

(56) References Cited

U.S. PATENT DOCUMENTS 6,200,257 B1 *   3/2001  Winkler ............... 600/3
2002/0165423 A1 * 11/2002 Forman ............... 600/3
(Continued)

FOREIGN PATENT DOCUMENTS

RU       2114563       7/1998

OTHER PUBLICATIONS

International Preliminary Report on Patentability and Written Opinion, dated Dec. 23, 2013, in connection with International Application No. PCT/US2012/043467.
(Continued)

*Primary Examiner* — Carrie R Dorna
(74) *Attorney, Agent, or Firm* — Meunier Carlin & Curfman LLC

(57) ABSTRACT

The present application relates to applicators and methods for administering therapeutic agents to cancerous tissue. The applicators can be used to deliver radiation and additional therapeutic agents to cancerous tissue located in a subject.

28 Claims, 3 Drawing Sheets

(56) References Cited

U.S. PATENT DOCUMENTS

| | | | |
|---|---|---|---|
| 2005/0004554 A1* | 1/2005 | Osborne | A61M 25/0068 604/524 |
| 2005/0080340 A1* | 4/2005 | Stewart et al. | 600/433 |
| 2006/0063962 A1 | 3/2006 | Drobnik et al. | |
| 2006/0173232 A1* | 8/2006 | Lovoi et al. | 600/1 |
| 2009/0234178 A1* | 9/2009 | Lebovic | A61N 5/1016 600/6 |
| 2010/0185173 A1* | 7/2010 | Popowski | A61N 5/1002 604/500 |
| 2010/0331815 A1 | 12/2010 | Alt | |

OTHER PUBLICATIONS

International Search Report, dated Oct. 11, 2012, in connection with International Application No. PCT/US2012/043467.

\* cited by examiner

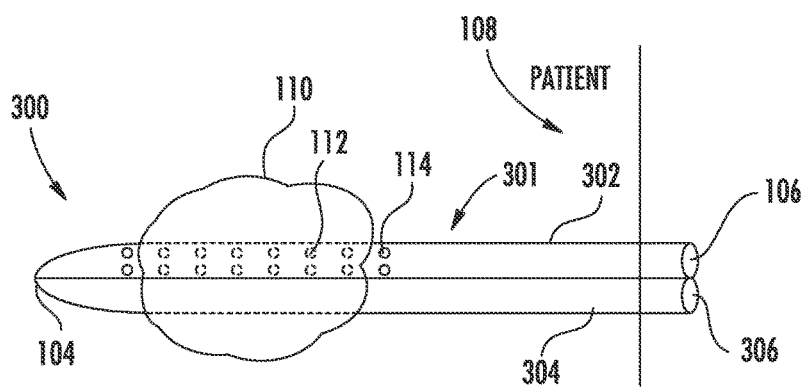
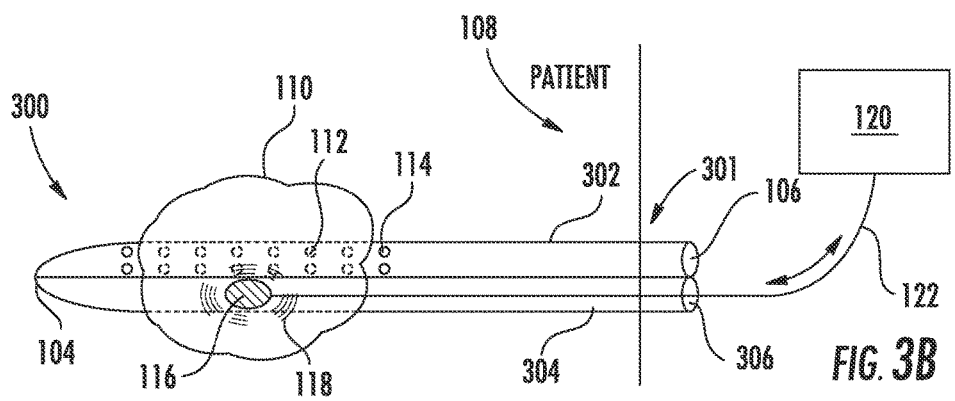
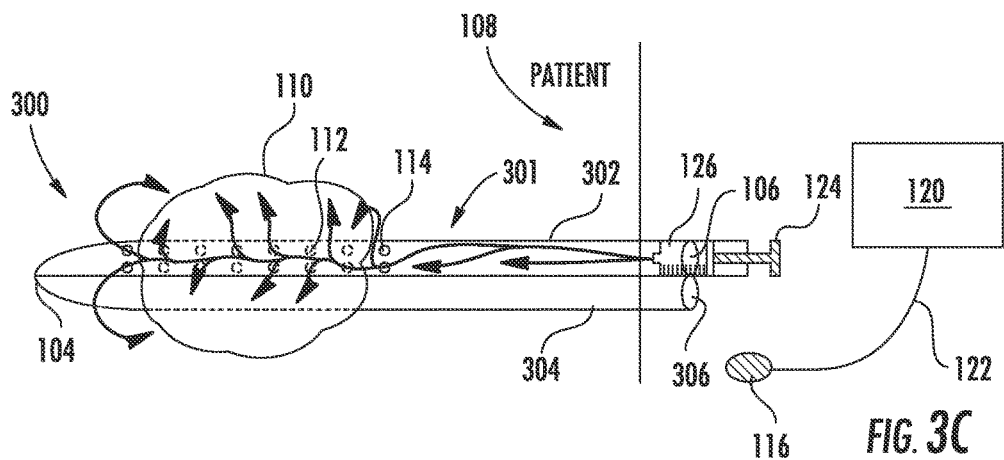

THERAPEUTIC AGENT APPLICATORS AND METHODS OF USING THE SAME

CROSS-REFERENCE TO PRIORITY APPLICATIONS

This application claims the benefit of U.S. Provisional Application No. 61/499,510, filed Jun. 21, 2011, which is incorporated herein by reference in its entirety.

TECHNICAL FIELD

The present application relates to applicators and methods for administering therapeutic agents to cancerous tissue.

BACKGROUND

Brachytherapy uses precisely delivered radiation sources to treat cancer within patients. The precise delivery of radiation sources is frequently accomplished by the placement of small applicators, however, or catheters into, or in proximity to, cancerous tissue. The placed applicators have not been effectively used for applying additional therapeutic approaches and agents to the irradiated cancer tissue.

SUMMARY

The present application relates to applicators and methods for administering therapeutic agents to cancerous tissue. The applicators can be used to deliver radiation and additional therapeutic agents to cancerous tissue located in a subject.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

FIGS. 3A-C are schematic illustrations of an example device for delivering a therapeutic agent to a subject.

DETAILED DESCRIPTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

The present application relates to applicators and methods for administering therapeutic agents to cancerous tissue. The applicators can be used to deliver radiation and additional therapeutic agents to cancerous tissue located in a subject.

Figure 1A:
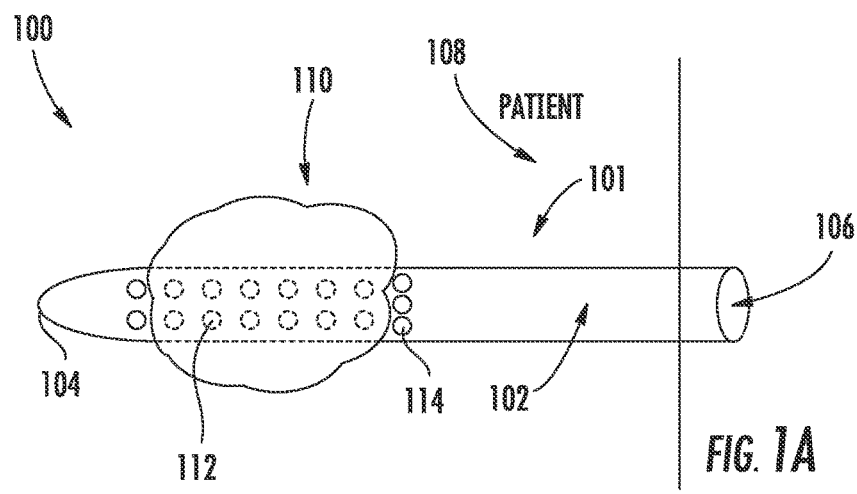
FIGS. 1A-C are schematic illustrations of an example device for delivering a therapeutic agent to a subject.
Figure 1B:
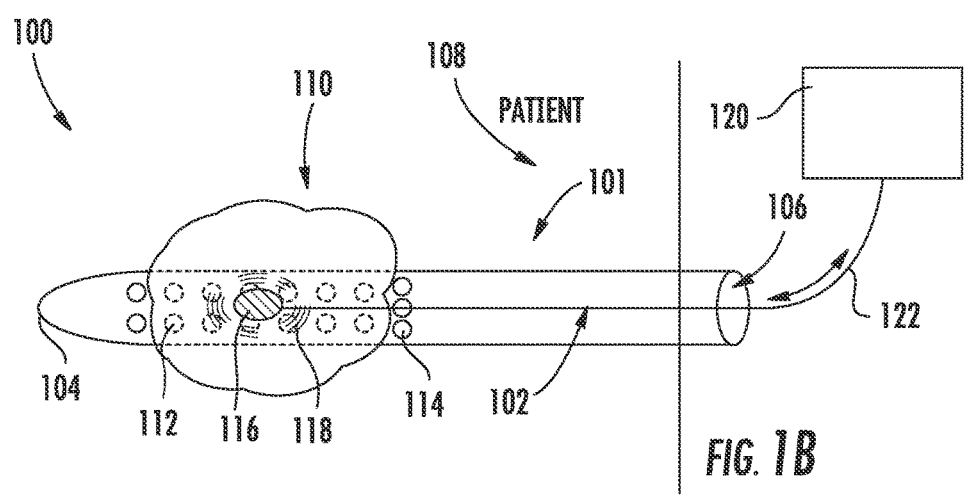
Figure 1C:
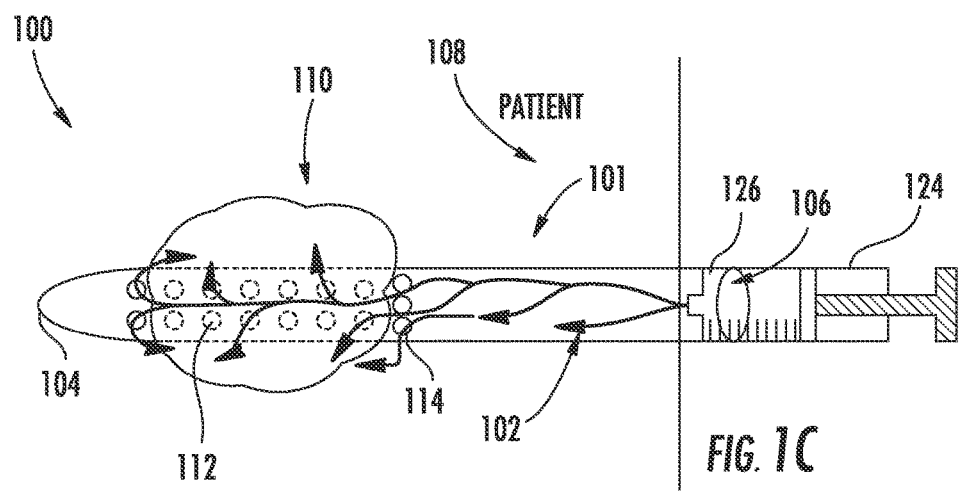

FIGS. 1A-C illustrates an example device 100 for administration of at least one therapeutic agent to cancerous tissue. As used herein, the term cancerous tissue includes any cancerous tissue of a subject, and would, therefore, include, for example, tumors, such as carcinomas and sarcomas. The cancerous tissue is optionally prostate cancer or breast cancer.

The device 100 comprises an applicator 101 with an elongate portion 102. The elongate portion 102 has a distal end 104. The distal end is optionally rounded or pointed to facilitate introduction of the applicator into and/or through normal or cancerous tissues 110 in the subject 108. The distal end is optionally closed.

The elongate portion 102 defines a lumen 106 configured to direct passage of the therapeutic agent towards the distal end. The applicator 101 further comprises at least one opening (112 and 114) spaced from the distal end 104 and in communication with the lumen 106. Each opening (112 and 114) is configured for directing the therapeutic agent from the lumen 106 to the cancerous tissue 110. The openings (112 and 114) may be any shape that allows passage of therapeutic agent from the lumen 106 and to the cancerous tissue 110. For example, the openings may optionally be round or oval.

Optionally, the applicator 101 comprises a plurality of openings (112 and 114), each spaced from the distal end 104 and in communication with the lumen 106. The plurality of openings can be positioned in a region of the applicator. Optionally, one or more opening is spaced by at least 0.5 inches from the distal end 104. The number of openings and the length of the region along the applicator can be varied depending, for example, on the tumor type and size being treated. The size of the openings can also vary. The size of the openings may also vary depending on, for example, tumor size, tumor type, therapeutic agent being used and pervious and/or future treatment regimens. For example, the openings may be one millimeter or larger in diameter.

In some examples, one or more openings 112 are positioned inside of the cancerous tissue 110 and one or more openings 114 are positioned outside of the cancerous tissue 110. In other examples, all of the openings are positioned inside of the cancerous tissue 110, and in still other examples, all of the openings are positioned outside of the cancerous tissue.

The tumor type, size and other patient and treatment factors can be readily determined using customary medical procedures such as, for example, medical imaging, physical exam, medical/treatment history and histopathology. Thus, a medical professional can select an applicator having a predetermined number, size and orientation of openings to provide a desired therapeutic effect. The desired therapeutic effect may include, but is not limited to, reducing the symptoms of the cancerous condition, a reduction in the severity of the cancerous condition, or the complete ablation of the cancerous condition.

Optionally, the applicator lumen 106 is further configured to direct passage of a radiation source 116 towards the distal end 104. To advance the radiation source 116 towards the distal end 104, an actuator 120 can be used. For example, the radiation source 116 may be engaged with the actuator 120 using a guide wire 122. The actuator 120 can comprise software and at least one processing unit to control advancement of the radiation source into, through and out of the lumen.

During use, the applicator 101 may house the radiation source 116 in, or in proximity to, its distal end 104. Portions of the applicator 101 in proximity to radiation 116 source allow radiation 118 to escape the applicator and to enter the cancerous tissue. For example, the radiation source 116 may be a brachytherapy seed for delivery of radiation therapy to cancerous tissue 110 of the subject.

Thus, the device 100 can be optionally used to deliver radiation therapy (e.g. brachytherapy) and the therapeutic agent. Optionally, the radiation therapy is administered prior to the therapeutic agent. Optionally, the therapeutic agent is selected from the group consisting of an immunotherapy agent, a dendritic cell, chemotherapy, biological agent, antibodies, immune cell, vaccine, and a cellular base immunotherapy. The therapeutic agent may comprise an aqueous or similar solution such that it may be flowably advanced through the lumen 106 and out of one or more opening (112 or 114).

Optionally, the applicator 101 is configured for intratumoral application of the therapeutic agent or of radiation from the radiation source 116. In this regard, the applicator 101 may be of sufficient rigidity to penetrate and/or to be advanced within a tumor. The desired rigidity may depend, for example, on the tumor type and tumor location. A rigid or semi-rigid stylet can be used to enhance the rigidity or to make the applicator sufficiently rigid for the desired application. The stylet can be optionally removed after insertion into or in proximity to the cancerous tissue.

Thus, the elongate portion 102 can be rigid or semi-rigid, and at least a portion of the elongate portion 102 can be configured for placement within the cancerous tissue 110. When positioned within the cancerous tissue 110, at least one opening (112 or 114) may be located within the cancerous tissue 110 thereby allowing direct intra-tumoral application of the therapeutic agent. Optionally, an inflatable balloon is positioned in proximity to the distal end. Such a configuration may be used in certain types of cancers, such as, for example, breast cancer. Optionally, the applicator is positioned in proximity to, but not in the cancerous tissue, which still allows direct application of the therapeutic agent to the cancerous tissue.

Prior to administration of the therapeutic agent the radiation source 116 is optionally removed from the applicator 101. Subsequent to removal, a source 124 of the therapeutic agent can be placed in communication with the applicator 101 such that the therapeutic agent can be advanced and expelled through at least one opening (112 and 114). An optional source of therapeutic agent is syringe 126, which can be connected to the applicator such that actuation of the syringe 126 forces therapeutic agent along the lumen and out of the opening under pressure. Other sources, such as medical fluid bags containing the therapeutic agent can also be used.

Referring now to FIG. 2, an example applicator 201 can comprise a second elongate portion 202 that defines a lumen 206 and that has a distal end 204. In this example, the second elongate portion 202 is configured for directing a radiation source 116 into proximity to the cancerous tissue 110 and the first elongate portion 102 is configured for directing a non-radiation therapeutic agent to the cancerous tissue.

Each elongate portion has a longitudinal axis, and the second elongate portion 202 is positionable within the lumen 106 of the first elongate portion 102 such that the longitudinal axes are substantially aligned. Thus, when the second elongate portion 202 is positioned within the lumen 106 of the first elongate portion 102 the two elongate portions are substantially co-axial with the portion configured to house and deliver the radiation source, e.g. elongate portion 206, positioned within the exterior portion, e.g. elongate portion 102, that delivers a non-radiation therapeutic agent.

Optionally, the second elongate portion 202 is removable or moveable from its position within the lumen 106 of the first elongate portion 102. Thus, the two elongate portions are optionally slideably moveable relative to each other. In other words, an inner portion for housing radiation can be slideably advanced or retraced within the lumen of the outer portion that delivers the non-radiation therapeutic agent.

In this regard, the radiation source 116 is positioned within the lumen 206 of the second elongate portion 202 when the second elongate portion is positioned within the lumen of the first elongate portion. Because the end of the second elongate portion 202 is closed, and because the second elongate portion does not have openings communicating with the lumen 106 of the first elongate portion 102, the lumen 206 housing the radiation source is closed from fluid communication with the lumen 106 of the first portion or with the patient's body 108.

Figure 2A:
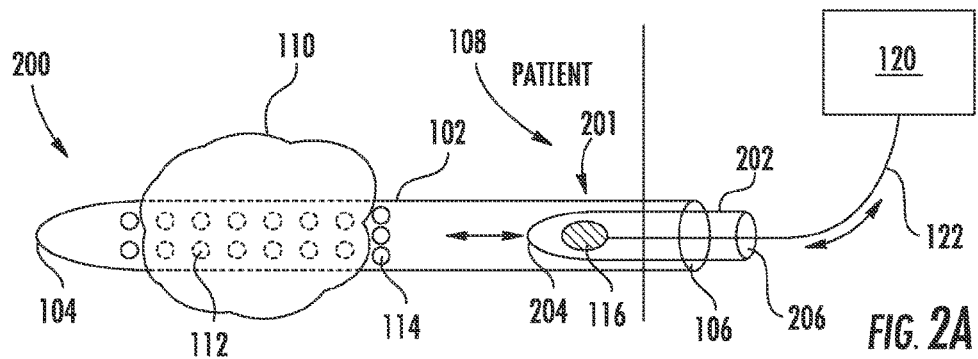
FIGS. 2A-D are schematic illustrations of an example device for delivering a therapeutic agent to a subject.
Figure 2B:
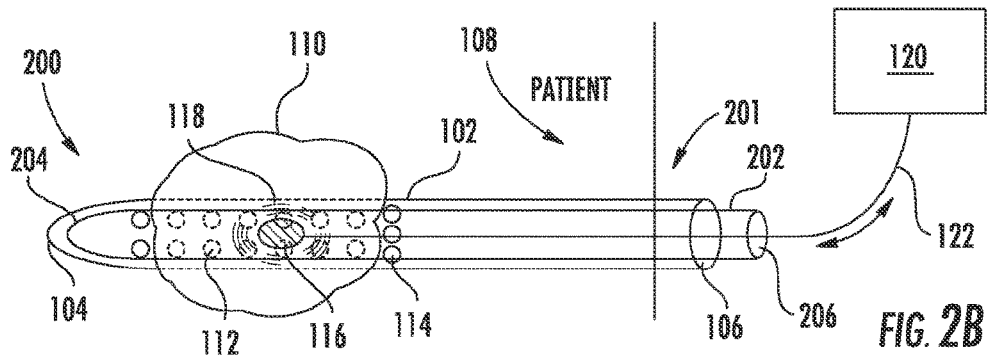
Figure 2C:
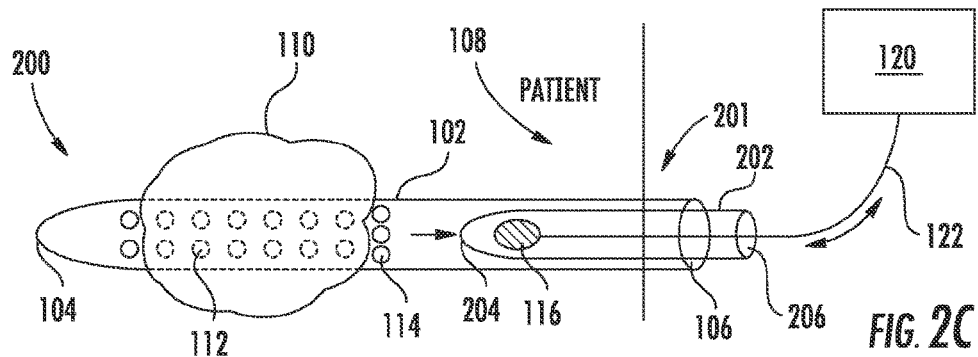

In practice, therefore, the two elongate portions, the second nested within the first, can be positioned in cancerous tissue 110 in the subject 108. As shown in FIG. 2B, the radiation source 116 can be advanced such that it can treat the cancerous tissue 110. As shown in FIG. 2C, the second elongate portion 202 and the radiation source 116 can then be removed from the first elongate portion 102, while the first elongate portion 102 remains within the cancerous tissue 110.

Figure 2D:
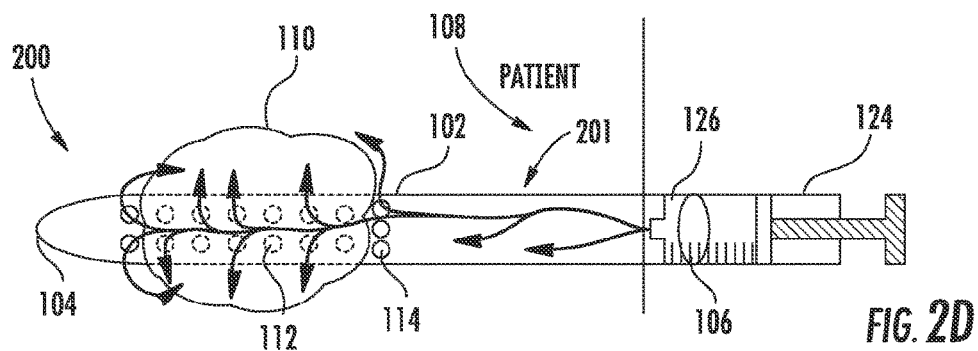

As shown in FIG. 2D, when the second elongate portion 202 is removed, therapeutic agent can be passed through the first, or outer, elongate portion 102. Since the elongate portion 102 comprises openings 112 and 114, the therapeutic agent can be delivered to the cancerous tissue 110 after the radiation was delivered. Thus, the device 200 allows for sequential administration of radiation and an additional therapeutic agent without contaminating the radiation source or guide wire 122.

Referring now to FIGS. 3A-C, a device 300 includes an applicator 301 having two elongate portions (302 and 304). Each elongate portion has a longitudinal axis that is spaced and substantially parallel to the longitudinal axis of the other portion. One of the elongate portions, e.g. portion 302, of the applicator 301 comprises one or more openings (112 and 114) spaced from the distal end 104. Each opening is in communication with the lumen 106, which is defined by the longitudinal portion 302.

The elongate portion 304 optionally has no openings and is configured to house a source of radiation 116 for treatment of the cancerous tissue 110. As described above, and as shown in FIG. 3B, the radiation source 116 is optionally advanced through the lumen 306 using an actuator 120 and a guide wire 122, which connects the actuator 120 and the radiation source 116.

In practice, a radiation source 116 can be positioned in the lumen 306 and advanced into a position such that radiation from the source can treat the cancerous tissue 110. After a predetermined time for radiation treatment, the radiation source 116 can be retracted from the lumen. During or after the radiation treatment, the therapeutic agent can be moved through the lumen 106 and out of the openings (112 and/or 114) to treat the cancerous tissue 110. Optionally, one or more opening (112 and/or 114) as described throughout can be valved such that release of therapeutic agent occurs when the valved opening is open, but such that release is prevented or reduced with the valve is closed.

The applicator for delivering the radiation source (101, 201, 301) can be a plastic brachytherapy catheter, or it can be made of another suitable material. The applicator can be directly inserted into the cancerous tissue or into subject tissue in proximity to the cancerous tissue. Example catheters can be obtained from Nucletron (Veenendall, N L). These catheters or similar tubes can be prepared with one or more of the described openings (112 or 114). The plastic catheters act as a conduit allowing a radiation source to be directly placed within the subject. Once the radiation treatment has been delivered the catheters are pulled out and no radioactive material is left within the subject.

A computer-controlled machine called the Flexitron® Robotic Afterloader (Nucletron, Veenendall, N L) is optionally used to push the radiation source 116, for example a radioactive iridium source, which is located on the end of a wire into the applicator. The radioactive source is then positioned at a number of "dwell" positions to deliver the radiation dose to the cancerous tissue. These positions can be determined with the aid of a planning computer allowing optimal dosage to the prostate. The treatment can be individually tailored to the patient's cancer and surrounding tissues by altering the dwell positions of the radioactive seed on the computer to give the best dose distribution within the cancerous tissue while reducing dosage to important anatomical structures.

Optionally, multiple applicators are placed in or in proximity to the cancerous tissue. The applicators may be placed under a general anesthetic under image guidance. For example, for prostate cancer, transrectal ultrasonography and X-ray imaging can be used.

Once the applicators are inserted, a CT scan can be made where imaging of the subject and applicator(s) is undertaken with subsequent computer planning allowing accurate calculation of the dose to be delivered and adjustment of the radioactive source positions. Once a plan has been completed, a radioactive source, which is housed in the afterloader, is delivered to the cancerous tissue.

Example 1: Placement of Applicators in Prostate Tissue

A patient was brought to the operating room where he was placed under general anesthesia. He was positioned in the lithotomy position and prepped and draped in sterile fashion. A transrectal ultrasound probe was introduced into the rectum and the prostate seminal vesicles were appropriately visualized. A Foley catheter was then introduced into the bladder under sterile conditions. A Stepper/Stabilizer was then moved up to the area of the perineum where a template was then secured onto it. Using template guidance via the transrectal ultrasound first interstitial needle/catheter was placed percutaneously via the template guide into the anterior portion of the prostate.

Once the applicator was felt to be in appropriate position on ultrasound a second applicator was then introduced in the adjacent prostate tissue. This was repeated for a total of 14 high dose rate interstitial plastic applicators. At the completion of positioning the applicator the template was locked and sutured onto the perineum. The ultrasound was then used again to verify positioning of the applicators with respect to the bladder and prostate. A fluoroscopic cystogram was then performed with 60 cc of 50/50 Conrad saline in the bladder and there was noted that there was no extravasation of the contrast material outside of the bladder. A Foley was set to drain on a bag and the patient was recovered from anesthesia.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for treatment of cancerous tissue, comprising:
   an applicator with a first elongate portion and a second elongate portion, each elongate portion terminating in a rigid distal end and each elongate portion defining a lumen, the distal end of the first elongate portion having sufficient rigidity to advance within the cancerous tissue without additional support;
   wherein the distal end of the first elongate portion is closed, thereby blocking its lumen, and wherein the first elongate portion is configured to direct passage of a therapeutic agent towards the distal end, wherein the first elongate portion further comprises at least one opening spaced from the closed distal end and in communication with the lumen of the first elongate portion, the at least one opening configured for directing the therapeutic agent from the lumen of the first elongate portion to the cancerous tissue;
   wherein the distal end of the second elongate portion is closed, thereby blocking its lumen, and wherein the second elongate portion is configured for directing a brachytherapy seed into proximity to the cancerous tissue, wherein the lumen of the first elongate portion and the lumen of the second elongate portion are not in fluid communication with each other;
   wherein each elongate portion has a longitudinal axis and wherein the second elongate portion is positioned within the lumen of the first elongate portion such that:
   (a) the longitudinal axes of the first and second lumens are substantially aligned;
   (b) the closed distal end of the first elongate portion prevents distal advancement of the second elongate portion beyond its distal end;
   (c) the distal end of the second elongate portion is proximal in relation to the longitudinal axis as compared to the distal end of the first elongate portion; and
   wherein the applicator comprising the first elongate portion and the second elongate portion are configured for simultaneous placement in, or in proximity to, the cancerous tissue.

2. The device of claim 1, wherein the first elongate portion comprises a plurality of the at least one opening, each spaced from the distal end and in communication with the lumen.

3. The device of claim 1 where the at least one opening is spaced by at least 0.5 inches from the distal end of the first elongate portion.

4. The device of claim 1, wherein the therapeutic agent is selected from the group consisting of an immunotherapy agent, a dendritic cell, chemotherapy, biological agent, antibodies, immune cell, vaccine, and a cellular base immunotherapy.

5. The device of claim 1, wherein the at least one opening is one millimeter or larger in diameter.

6. The device of claim 1, wherein the applicator is configured for intra-tumoral application.

7. The device of claim 1, wherein an inflatable balloon is positioned in proximity to the distal end of the first elongate portion.

8. The device of claim 1, wherein the therapeutic agent is in aqueous solution.

9. The device of claim 1, wherein the at least one opening is located in a region beginning a fixed distance from the distal end of the first elongate portion and ending a fixed distance from the distal end of the first elongate portion.

10. The device of claim 1, wherein the applicator is configured to expel the therapeutic agent through the at least one opening.

11. The device of claim 1, wherein the second elongate portion is removable from its position within the lumen of the first elongate portion.

12. The device of claim 1, wherein the brachytherapy seed is positioned within the lumen of the second elongate portion.

13. The device of claim 1, wherein one or more of the at least one opening is valved.

14. The device of claim 1, wherein the first elongate portion is rigid or semi-rigid.

15. The device of claim 1, wherein the second elongate portion is rigid or semi-rigid.

16. The device of claim 1, wherein at least a portion of the applicator is configured for placement within the cancerous tissue.

17. The device of claim 16, wherein the portion of the applicator within the cancerous tissue comprises the at least one opening spaced from the distal end of the first elongate portion.

18. The device of claim 17, wherein the portion of the applicator within the cancerous tissue houses at least one brachytherapy seed.

19. The device of claim 18, wherein the cancerous tissue comprises prostate cancer or breast cancer.

20. A method for treating cancerous tissue comprising:
 positioning the applicator according to claim 1 in, or in proximity to, the cancerous tissue;
 advancing the radiation source through the second elongate portion of the applicator to a position where it irradiates at least a portion of the cancerous tissue; and
 administering the therapeutic agent using the first elongate portion to the irradiated cancerous tissue, wherein the administration is performed directly to the irradiated cancer tissue.

21. The method of claim 20, wherein the cancerous tissue comprises prostate cancer or breast cancer.

22. The method of claim 20, wherein the therapeutic agent is selected from the group consisting of an immunotherapy agent, a dendritic cell, chemotherapy, biological agent, antibodies, immune cell, vaccine, and a cellular base immunotherapy.

23. The device of claim 1, further comprising a stylet at the distal end of the first elongate portion.

24. The device of claim 1, the stylet having sufficient rigidity to penetrate the cancerous tissue.

25. The device of claim 23, wherein the stylet is removable from the distal end of the first elongate portion.

26. The device of claim 1, wherein rigidity of the distal end of the first elongate portion corresponds to characteristics of the cancerous tissue.

27. The device of claim 1, wherein the distal end of the first elongate portion is rounded.

28. The device of claim 1, wherein the distal end of the first elongate portion is rounded.

* * * * *